US010212935B2

(12) United States Patent
Uhr et al.

(10) Patent No.: US 10,212,935 B2
(45) Date of Patent: Feb. 26, 2019

(54) BIOCIDIC MICROCAPSULES

(71) Applicant: LANXESS Deutschland GmbH, Cologne (DE)

(72) Inventors: Hermann Uhr, Leverkusen (DE); Katrin Moews, Dortmund (DE); Monika Lamoratta, Langenfeld (DE)

(73) Assignee: LANXESS Deutschland GmbH, Cologne (DE)

( * ) Notice: Subject to any disclaimer, the term of this patent is extended or adjusted under 35 U.S.C. 154(b) by 42 days.

(21) Appl. No.: 15/121,393

(22) PCT Filed: Feb. 25, 2015

(86) PCT No.: PCT/EP2015/053942
§ 371 (c)(1),
(2) Date: Aug. 25, 2016

(87) PCT Pub. No.: WO2015/128382
PCT Pub. Date: Sep. 3, 2015

(65) Prior Publication Data
US 2016/0360753 A1  Dec. 15, 2016

(30) Foreign Application Priority Data
Feb. 27, 2014 (EP) .................................... 14157006

(51) Int. Cl.
*A01N 47/12* (2006.01)
*A01N 25/28* (2006.01)
*C09D 5/14* (2006.01)
*C09D 161/28* (2006.01)
*C09D 7/40* (2018.01)
*C08K 5/00* (2006.01)
*C08K 9/10* (2006.01)

(52) U.S. Cl.
CPC ............ *A01N 47/12* (2013.01); *A01N 25/28* (2013.01); *C09D 5/14* (2013.01); *C09D 7/69* (2018.01); *C09D 161/28* (2013.01); *C08K 5/0058* (2013.01); *C08K 9/10* (2013.01)

(58) Field of Classification Search
None
See application file for complete search history.

(56) References Cited

U.S. PATENT DOCUMENTS

| 7,429,392 B2 | 9/2008 | Baum et al. |
| 2005/0003205 A1 | 1/2005 | Wachtler et al. |
| 2010/0099793 A1 | 4/2010 | Wunder |
| 2013/0197127 A1* | 8/2013 | Wilken .................... C09D 5/14 523/122 |

FOREIGN PATENT DOCUMENTS

| EP | 0758633 A1 | 2/1997 |
| JP | 2002053412 A2 | 2/2002 |
| JP | 2004099557 A2 | 4/2004 |
| WO | 2008000797 A2 | 1/2008 |

OTHER PUBLICATIONS

Finch, Christopher A., et al., "Microencapsulation", 2005 Wiley-VCH Verlag GmbH, pp. 1-16.
Wan, Asma Ibrahim, et al., "Performance of Microencapsulated Fungicide in Exterior Latex Pain on Wood Substrate", Pertanika 12(3), 1989, pp. 409-412.
International Search Report from International Application No. PCT/EP2015/053942, dated Apr. 30, 2015, three pages.

* cited by examiner

*Primary Examiner* — Robert T Butcher

(57) ABSTRACT

The present invention relates to microcapsules comprising one or more biocides such as, in particular, iodopropargyl compounds, and at least one melamine-formaldehyde polymer, to a process for producing such microcapsules, and to their use for protecting technical materials.

19 Claims, No Drawings

BIOCIDIC MICROCAPSULES

The present invention relates to microcapsules comprising one or more biocides such as, in particular, iodopropargyl compounds, and at least one melamine-formaldehyde polymer, to a process for producing such microcapsules, and to their use for protecting technical materials.

BACKGROUND INFORMATION

Iodopropargyl compounds are known active ingredients which are used particularly in material protection for protecting technical materials such as adhesives, sizes, paper and cardboard, textiles, leather, wood, woodbase materials, coatings and plastic articles, cooling lubricants and other materials which can be attacked or decomposed by microorganisms against attack, particularly by fungi. The best known representative of the iodopropargyl compounds is iodopropargyl butylcarbamate, which is also referred to hereinbelow as IPBC.

High demands are placed on fungicides used for the finishing of coating compositions such as e.g. wood protection paints, exterior paints or plasters. For example, the fungicidally finished coating compositions have to remain stable even upon frequent contact with water and must not be subject to any undesired discolouration. Since some fungicides such as, for example, IPBC, have a certain solubility in water, as a result of contact of the exterior paint for example with driving rain, the fungicide is washed out of the paints. This process is also called "leaching". It results in a reduction in the fungitoxic effect in the coating compositions as well as a severe local burden on the environment by the active ingredients or their metabolites. This leaching should be low so that the coating compositions and the exterior walls are protected against fungal attack for a long time. One option of reducing the leaching is to use microencapsulations.

Coating compositions protected against microbiological attack, and processes for producing microencapsulated biocides are known from the prior art.

Thus, for example, WO 04/000953A1 describes a coating composition for protecting against microorganism attack of surfaces which are subjected to the action of moisture or water, wherein the coating composition either itself has a pH of at least 11.0 or is intended for the coating of a substrate material whose pH is at least 11.0. The coating composition is characterized in that it comprises a biocide, such as e.g. IPBC, which is bonded in a carrier material made of solids particles and is released therefrom in a delayed manner.

DE102006061890 A1 describes sealing compositions which comprise, as biocide, for example 2-n-octyl-4-isothiazolin-3-one and optionally one or more other biocides, wherein the biocide is enclosed in microparticles made, for example, of an aminoplastic resin.

It is known from DE10133545 A1 to treat sealing compositions with special benzothiophene fungicide preparations in order to prevent the polymer masses from becoming mouldy. Reference is also made here to the difficulty of finding suitable fungicides for sealing compositions which are stable and are not subject to being washed out. Consequently, the biocides employed have to be used in high concentrations, which can also lead to an environmental impact.

It is known from JP2002-053412 A2 that biocides can be enclosed in a resin matrix. Thus, the inclusion of 2-n-octyl-4-isothiazolin-3-one in a styrene-maleic anhydride resin is described in this document, EP 0 758 633 A1 describes porous granules which can comprise chemical substances, such as, for example, also biocides, which slowly release these during use.

JP2004039557 A2 describes fine particles of biocide-containing resin which are used for suppressing the growth of microorganisms especially in aqueous emulsion paints.

However, the microcapsules known from the prior art still have no satisfactory antifungal effect coupled with simultaneously low leaching rate and high resistance or storage stability.

It was therefore the object of the present invention to provide microcapsules which permit improved protection of coating compositions against fungal attack.

SUMMARY

The solution to the stated problem and the subject matter of the present invention are then microcapsules comprising at least one iodopropargyl compound, where the at least one iodopropargyl compound is microencapsulated with a microencapsulation material which comprises at least one melamine-formaldehyde polymer.

The scope of the invention encompasses all of the parameters and explanations above and below, specified in general terms or within preferred ranges, with one another, i.e. also between the respective ranges and preferred ranges in any desired combination.

DESCRIPTION OF THE EMBODIMENTS

The microcapsules according to the invention comprise at least one iodopropargyl compound which is selected from the group:

3-iode-2-propynyl propylcarbamate, 3-iodo-2-propynyl butylcarbamate (IPBC), 3-iodo-2-propynyl m-chlorophanylcarbamate, 3-iodo-2-propynyl phenylcarbamate, 3-iodo-2-propynyl 2,4,5-trichlorophenyl ether, 3-iodo-2-propynyl 4-chlorophenyl formal (IPCF), di-(3-iodo-2-propynyl)hexyl dicarbamate, 3-iodo-2-propynyl oxyethanol ethylcarbamate, 3-iodo-2-propynyl oxyethanol phenylcarbamate, 3-iodo-2-propynyl thioxothioethylcarbamate, 3-iodo-2-propynyl carbamic add ester (IPC), N-iodopropargyloxycarbonylalanine, N-iodopropargyloxycarbonylalanine ethyl ester, 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-bromo-2,3-diiodo-2-propenylethyl carbamate, 3-iodo-2-propynyl-n-hexyl carbamate, 3-iodo-2-propynyl cyclohexyl carbamate.

A particularly preferred iodopropargyl compound is 3-iodo-2-propynyl butylcarbamate (IPBC).

The iodopropargyl compounds themselves are known and can be prepared by methods known in the literature or be acquired commercially.

The microencapsulation of the iodopropargyl compounds takes place by means of a microencapsulation material. In the context of this invention, microencapsulation means the at least partial, preferably complete covering of the at least one iodopropargyl compound with microencapsulation material.

The microcapsules according to the invention have, for example, a volume-average particle size of from 0.3 to 100 μm, preferably from 5 to 60 μm.

In a further embodiment, the microcapsules according to the invention have, for example, a D90 value, determined by a laser diffraction as volume-weighted distribution as described in the experimental section, of 90 μm or less, preferably 60 μm or less, particularly preferably 10 to 60 μm.

The microcapsules according to the invention comprise at least one melamine formaldehyde polymer as microencapsulation material. The term melamine-formaldehyde polymer is to be understood as meaning a polymer which is a polycondensate of at least melamine and formaldehyde. Such polycondensates are typically obtained by polycondensation of melamine with a molar excess of formaldehyde.

General processes for producing microcapsules, in particular also for producing microcapsules of melamine-formaldehyde polycondensates, are known (see for example C. A. Finch, R. Bodmeier, Microencapsulation, Ullmann's Encyclopedia of Industrial Chemistry, $6^{th}$ edition 2001, Electronic Release).

The microcapsules according to the invention can, for example, comprise at least one further microencapsulation material which is selected from the group of synthetic, semisynthetic or natural polymers, such as in particular aminoplastic resins.

Aminoplastic resins are generally understood as meaning polycondensation products of carbonyl compounds with compounds containing NH groups. Of particular interest in this connection are melamine-formaldehyde resins modified with urea or phenyl (melamine-urea-formaldehyde resins, melamine-phenol-formaldehyde resins). As further possible aminoplastic resins, it is possible to add, for example, aminoplastic resins of a compound containing NH groups and acetaldehyde or glyoxal to the melamine-formaldehyde resin.

Furthermore, the microencapsulation material can comprise urethane resins, cyanamide resins or dicyanamide resins, aniline resins, sulphonamide resins or mixtures of these resins. Such resins and their production are known to the person skilled in the art.

Preferred synthetic polymers are, for example, acrylic polymers and copolymers, polyacrylamide, polyalkyl cyanoacrylate, and polyethylene vinyl acetate), aluminium monostearate, carboxyvinyl polymers, polyamides, poly(methyl vinyl ether-maleic anhydride), poly(adipyl-L-lysine), polycarbonates, polyterephthalamide, polyvinyl acetate phthalate), poly(terephthaloyl-L-lysine), polyarylsulphones, poly(methyl methacrylate), poly-(ε-caprolactone), polyvinylpyrrolidone, polydimethylsiloxane, polyoxyethylenes, polyesters, polyglycolic acid, polylactic acid and copolymers thereof, polyglutamic acid, polylysine, polystyrene, poly(styrene-acrylonitrile), polyimides and polyvinyl alcohol.

Preferred semisynthetic polymers are, for example, cellulose acetate, cellulose acetate butyrate, cellulose acetate phthalate, cellulose nitrate, ethylcellulose, hydroxypropylcellulose, sodium carboxymethylcellulose, hydroxypropylmethylcellulose, methylcellulose, hydroxypropylmethylcellulose phthalate, hydrogenated tallow, myristyl alcohol, glycerol mono- or dipalmitate, hydrogenated castor oil, glyceryl mono- or tristearates and 12-hydroxystearyl alcohol.

Preferred natural polymers are, for example, gum arable, agar, agarose, maltodextrin, sodium alginate, calcium alginate, dextran, fats, fatty acids, cetyl alcohol, milk solids, molasses, gelatine, gluten, albumin, shellac, starches, caseinates, steams, sucrose, and waxes such as beeswax, carnauba wax and spermaceti wax.

In general, besides at least one melamine-formaldehyde polymer, the microencapsulation material can comprise, based on its total weight, up to 60% by weight of other synthetic or semisynthetic or natural polymers, such as in particular aminoplastic resins.

Preferably, the microencapsulation material comprises at least 95% by weight of at least one melamine-formaldehyde polymer, particularly preferably at least 99% by weight of at least one melamine-formaldehyde polymer.

In general, the weight ratio (w/w) of the microencapsulation material to the at least one iodopropargyl compound in the microcapsules according to the invention is from 1:10 to 100:1, preferably from 1:10 to 10:1 and very particularly preferably from 1:4 to 2:1.

Also encompassed by the invention is a process for producing the microcapsules according to the invention, characterized in that it at least comprises:
a) application of microencapsulation material comprising at least one melamine-formaldehyde polymer to at least one iodopropargyl compound
b) treatment at a temperature T of from 50 to 95° C., preferably 64 to 95° C., preferably 68 to 95° C., particularly preferably 70 to 95° C. and very particularly preferably 70 to 90° C., over a period t, such that the product T×T×t is>18 000, preferably >20 000 and particularly preferably >25 000 (° C.)$^2$h.

According to a), the at least one melamine-formaldehyde polymer is applied to the at least one iodopropargyl compound.

Melamine-formaldehyde polymers suitable for this are sufficiently known and commercially available for example under the trade names Saduren® (BASF AG), Maprenal® (Ineos Melamines), Quecodur® (Thor GmbH) or can be produced from melamine and formaldehyde by methods known per se, as described for example in WO 2006/000797 A2.

The application in a) is preferably carried out in such a way that an aqueous emulsion or suspension of the at least one iodopropargyl compound is brought into contact with at least one melamine-formaldehyde polymer, preferably dissolved in an aqueous medium, and the application of the at least one melamine-formaldehyde polymer to the at least one iodopropargyl compound is brought about by reducing the solubility of the at least one melamine-formaldehyde polymer.

The reduction in the solubility can take place here either by increasing the electrolyte content, such as e.g. by adding sail or an aqueous salt solution, or by adjusting the pH.

Suitable conditions for the application of the polymer to the iodopropargyl compounds can be determined experimentally in a few preliminary experiments without major effort. For example, the application can take place at a pH in the range from 0 to 6.5, preferably from 1.0 to 4.0, particularly preferably from 2.50 to 3.50 and very particularly preferably from 2.80 to 3.20 measured or based on standard conditions.

In the process according to the invention for producing the microcapsules according to the invention, the application of the melamine-formaldehyde polymers can take place within a wide temperature range, for example the application takes place at a temperature of from 10 to 95° C., preferably from 50 to 96° C., particularly preferably in a range from 64 to 95° C., very particularly preferably at a temperature of 68 to 95° C., even further preferably at a temperature of 70 to 95° C. and very particularly preferably at 70 to 95° C. Particularly when using IPBC, temperatures are from 68 to 95° C., preferably 70 to 95° C. and particularly preferably 70 to 90° C. are advantageous since they are at the upper end of the melting point range of IPBC or above (64-68° C.).

The bringing into contact and application can, for example, take place such that an aqueous emulsion or suspension of the at least one iodopropargyl compound is initially introduced and an aqueous solution of at least one melamine-formaldehyde polymer is added, before then the reduction in the solubility of the at least one melamine-formaldehyde polymer takes place, preferably by adjusting the pH.

In this case, the addition of the electrolyte or the adjustment of the pH takes place, for example, directly or over a period of at least one minute, preferably over a period of at least 30 minutes to 24 hours, particularly preferably over a period of at least one hour and very particularly preferably over a period of at least 2 to 6 hours.

Alternatively to this, the bringing into contact and application can, for example, take place such that an aqueous emulsion or suspension of the at least one iodopropargyl compound is provided in which conditions are established which bring about the application of at least one melamine-formaldehyde polymer, preferably by adjusting the pH, and then an aqueous solution of at least one melamine-formaldehyde polymer is added.

To establish the pH, either inorganic or organic acids, such as, for example, hydrochloric acid, sulphuric acid, phosphoric acid or citric acid, oxalic add, acetic acid, formic acid, acidic salts or any desired mixtures of the aforementioned compounds, can be used.

Iodopropargyl compounds are typically only poorly soluble in water.

In a), therefore, preferably aqueous emulsions or suspensions of Iodopropargyl compounds, or solutions of iodopropargyl compounds in an organic solvent are used. In this connection, it is clear to the person skilled in the art that in order to produce emulsions of iodopropargyl compounds in an organic solvent, it is necessary to use those organic solvents which are immiscible or at least not completely miscible with water.

In a particularly preferred embodiment, in step a), an aqueous suspension of at least one iodopropargyl compound is used.

In an alternative embodiment, an aqueous, emulsified melt of at least one iodopropargyl compound is used.

In a), further auxiliaries known to the person skilled in the art can also be added to the aqueous emulsion or suspension, such as, for example, protective colloids.

Suitable protective colloids are, for example, polyacrylates, preferably Coadis® BR3 (Coatex), partially saponified polyvinyl acetate, polyvinyl alcohol, polyvinylpyrolidone, cellulose ether (Tylose), such as, for example, methylcellulose, hydroxyethylcellulose or hydroxypropylmethylcellulose, starch, proteins, gum arabic, alginates, pectins, gelatines or mixtures of these compounds. Particular preference is given to using a mixture of gum arabic and polyacrylate as protective colloid.

The protective colloid is typically at least partially a constituent of the microencapsulation material as described above.

In the process according to the invention for producing the microcapsules according to the invention, according to b), a treatment temperature T of from 50 to 95° C., preferably 64 to 95° C., preferably 88 to 95° C., particularly preferably 70 to 95° C. and very particularly preferably 70 to 90° C., takes place over a period t, such that the product $T \times T \times t$ is >18 000, preferably >20 000, such as for example >20 000 to 300 000 and particularly preferably >25 000, such as for example >25 000 to 300 000 (° C.)$^2$h. Treatment at a certain temperature is to be understood as meaning the treatment of microcapsules as soon as they are formed according to a), i.e. from the start of the application of microencapsulation material. The feature according to b) is accordingly already satisfied when the application temperature is in the aforementioned temperature interval.

The treatment according to b) can take place alternatively or additionally when the application is complete also by exposing the microcapsules to a temperature which is within the stated intervals. This exposure can take place for example and preferably by post-stirring, leaving to stand or storage of the reaction mixtures, or take place following isolation of the microcapsules for example by storage.

Without wishing to be scientifically committed in any way, it is assumed that as a result of the treatment at the aforementioned temperatures, any groups that are still not crosslinked or still not polymerized become crosslinked or polymerized.

The treatment at the aforementioned temperatures preferably takes place over a period of one hour or more, preferably over a period from 1 to 30 hours, particularly preferably over a period from 5 to 30 hours.

Longer periods no longer afford noteworthy improvements.

in a preferred embodiment, the treatment and the above product refers to the period and the temperature after the application is complete.

In an alternative embodiment, it is possible to add urea to a suspension or emulsion of the iodopropargyl compounds for producing the microcapsules according to the invention. The urea addition can take place for example prior to the treatment according to b). In an alternative embodiment, the addition of the urea can also take place directly after the treatment according to b). In a further alternative embodiment, the addition of the urea can take place in the course of a formulation with further auxiliaries such as, for example, pack preservatives and emulsifiers after the thermal treatment. Preferably, the addition of the urea takes place after the thermal treatment in the course of a formulation with further auxiliaries.

The addition of the urea can also take place during the production of the formulation from the isolated microcapsules.

The added amount of urea is, for example, from 0.1 to 20% by weight, preferably 1 to 10% by weight, particularly preferably 2 to 5% by weight, based on the total amount of encapsulation material used.

The process according to the invention for producing the microcapsules according to the invention can be carried out at any desired pressures. Preferably, the process according to the invention for producing the microcapsules according to the invention is carried out at ambient pressure.

The microcapsules according to the invention can then be isolated for example by filtration, sedimentation or centrifugation, and optionally dried at room temperature or by gentle heating. However, there is also the option to dry and to isolate the microencapsulation material by spray drying or freeze drying. Preferably, the microcapsules according to the invention are separated off by filtration and used without further drying for producing formulations.

The microcapsules that can be produced according to the invention surprisingly have a reduced leaching rate compared to other microencapsulation processes, and are therefore particularly advantageous.

Consequently, the invention furthermore encompasses microcapsules which are obtainable by the process according to the invention and/or microcapsules comprising at least one iodopropargyl compound, where the at least one iodopropargyl compound is microencapsulated with at least one melamine-formaldehyde polymer and where the microcapsules have a 24 h leaching rate of 1 to 80 ppm (ppm unless stated otherwise always refers to ppm by weight), preferably from 2 to 50 ppm, particularly preferably from 5 to 40 ppm and very particularly preferably 5 to 30 ppm, determined by means of 24 h leaching test, as given in the examples.

The microcapsules according to the invention are particularly suitable for use in or as biocides, in particular fungicidal agents. Consequently, the invention also encompasses biocidal agents comprising microcapsules according to the invention, as well as the use of the microcapsules according to the invention as biocidal agent or in biocidal agents.

The microcapsules according to the invention are characterized by high efficacy and their broad activity spectrum towards fungi.

By way of example, mention may be made of microorganisms of the following genus:
*Alternaria,* such as *Alternaria tennis,*
*Aspergillus,* such as *Aspergillus vigor,*
*Chaetomium,* such as *Chaetomium globosum,*
*Coniophora,* such as *Coniophora puetana,*
*Lentinus,* such as *Lentinus tigrinus,*
*Penicillium,* such as *Penicillium glaucum,*
*Polyporus,* such as *Polyporus versicolor,*
*Aureobasidium,* such as *Aureobasidium pullulans,*
*Sclerophoma,* such as *Sclerophoma pityophila,*
*Trichoderma,* such as *Trichoderma viride.*

The biocidal agents according to the invention can be present in any desired formulation, such as, for example, in the form of suspension concentrates, water-dispersible powders, water-dispersible granules or simple powder mixtures, preference being given to suspension concentrates, powder mixtures and water-dispersible granules.

In principle, preferred types of formulation are essentially dependent on the intended use and the physical properties required for this. However, since these are known, it is customary practice for the person skilled in the art to ascertain a preferred type of formulation in a few experiments.

The formulations can also comprise further substances, such as stabilizers, pack preservatives and further biocides, such as, for example, fungicides, algicides, insecticides, acaricides, nematicides, radicides and herbicides or mixtures thereof, preferably fungicides or algicides, or mixtures thereof, very preferably algicides, in each case independently of one another either in microencapsulated form or non-microencapsulated form.

Besides the microcapsules according to the invention, the biocidal agents can optionally further comprise various auxiliaries. For the auxiliaries specified below, there is in each case, independently of the others, also the option that they are not present. Possible auxiliaries are for example:

interface-active substances, such as, for example, surfactants. Surfactants may be, for example, non-ionic, cationic and amphoteric surfactants, preferably anionic surfactants. Anionic surfactants are, for example, alkyl sulphates, alkyl ether sulphates, alkylarylsulphonates, alkyl succinates, alkyl sulphosuccinates, N-alkoyl sarcosinates, acyl taurates, acyl isethionates, alkyl phosphates, alkyl ether phosphates, alkyl ether carboxylates, alpha-olefinsulphonates, in particular the alkali metal and alkaline earth metal salts, for example sodium, potassium, magnesium, calcium, and also ammonium and triethanolamine salts. The alkyl ether sulphates, alkyl ether phosphates and alkyl ether carboxylates can in each case have for example from 1 to 10 ethylene oxide or propylene oxide units, preferably 1 to 3 ethylene oxide units. Sodium lauryl sulphate, ammonium lauryl sulphate, sodium lauryl ether sulphate, ammonium lauryl ether sulphate, sodium lauryl sarcosinate, sodium oleyl succinate, ammonium lauryl sulphosuccinate, sodium dodecyl benzenesulphonate, triethanolamine dodecylbenzenesulphonate, for example, are suitable. The biocidal agents according to the invention can comprise here, for example, from 0.01 to 10% by weight, preferably from 0.2 to 8% by weight, particularly preferably from 0.3 to 5% by weight and very particularly preferably from 0.5 to 3% by weight, of interface-active substances.

Antifoams. The antifoams used are generally interface-active substances which are weakly soluble in the surface-active solution. Preferred antifoams are those which are derived from natural fats and oils, petroleum derivatives or silicone oils.

Wetting agents, such as, for example, alkali metal, alkaline earth metal, ammonium salts of aromatic sulphonic adds, for example lignin-, phenol-, naphthalene- and dibutylnaphthelenesulphonic add, and also of fatty adds, alkyl- and alkylarylsulphonetes, alkyl, lauryl ether and fatty alcohol sulphates, and salts of sulphated hexa-, hepta- and octedecanols or fatty alcohol glycol ethers, condensation products of sulphonated naphthalene and its derivatives with formaldehyde, condensation products of naphthalene or of naphthalene sulphonic adds with phenol and formaldehyde, polyoxyethylene octyl phenol ether, ethoxylated isooctyl-, octyl- or nonylphenol, alkylphenol or tributylphenyl polyglycol ether, trissteryl phenyl ether ethoxylates, alkylaryl polyether alcohols, isotridecyl alcohol, fatty alcohol ethylene oxide condensates, ethoxylated castor oil, polyoxyethylene alkyl ether and polyoxypropylene, lauryl alcohol polyglycol ether acetate, sorbitan esters, lignosulphite waste liquors or methylcellulose. The biocidal agents according to the invention here can comprise, for example, from 0.01 to 8% by weight, preferably from 0.2 to 6% by weight, particularly preferably from 0.3 to 5% by weight and very particularly preferably from 0.5 to 3% by weight, of wetting agents.

Emulsifiers, such as, for example, sodium, potassium and ammonium salts of straight-chain aliphatic carboxylic adds of chain length $C_{10}$-$C_{20}$. Sodium hydroxyoctadecanesulphonate, sodium, potassium and ammonium salts of hydroxy fatty adds of chain length $C_{10}$-$C_{20}$ and their sulphation or acetylation products, alkyl sulphates, also as triethanolamine salts, alkyl-($C_{10}$-$C_{20}$)-sulphonates, alkyl-($C_{10}$-$C_{20}$)-arylsulphonates, dimethyldialkyl-($C_8$-$C_{18}$)-ammonium chloride, acyl, alkyl, oleyl and alkylaryl oxethylates and their sulphation products, alkali metal salts of sulphosuccinc acid esters with aliphatic saturated monohydric alcohols of chain length $C_4$-$C_{18}$, sulphosuccinic acid 4-esters with polyethylene glycol ethers of monohydric aliphatic alcohols of chain length $C_{10}$-$C_{12}$ (disodium salt), sulphosuccinic acid 4-esters with polyethylene glycol nonyl phenyl ether (disodium salt), sulphosuccinic acid bis-cyclohexyl ester (sodium salt), ligninosulphonic acid, and calcium, magnesium, sodium and ammonium salts thereof, polyoxyethylene sorbitan monooleate with 20 ethylene oxide groups, resin acids, hydrogenated and dehydrogenated resin acids, and alkali metal salts thereof, dodecylated diphenyl ether disulphonic acid sodium, and copolymers of ethylene oxide and propylene oxide with a minimum content of 10% by weight ethylene oxide. Preferably, the emulsifiers used are: sodium lauryl sulphate, sodium lauryl ether sulphate, ethoxylated (3 ethylene oxide groups); the polyethylene glycol (4-20) ethers of oleyl alcohol, and the polyethene oxide (4-14) ethers of nonylphenol. The biocidal agents according to the invention can here comprise, for example, from 0.01 to 15% by weight, preferably from 0.02 to 8% by weight, particularly preferably from 0.05 to 6% by weight and very particularly preferably from 0.1 to 5% by weight, of emulsifiers.

Dispersants, such as, for example, alkylphenol polyglycol ethers. The biocidel agents according to the invention can here comprise, for example, from 0.01 to 15% by weight, preferably from 0.02 to 8% by weight, particularly preferably from 0.06 to 6% by weight and very particularly preferably from 0.1 to 5% by weight, of dispersants.

Stabilizers, such as, for example, cellulose and cellulose derivatives. The biocidal agents according to the invention can comprise here, for example, from 0.01 to 6% by weight, preferably from 0.01 to 3% by weight, particularly preferably from 0.01 to 2% by weight and very particularly preferably from 0.01 to 1% by weight, of stabilizers.

Stabilizers, such as, for example, antioxidants, free-radical scavengers or UV absorbers.

Adhesives or protective colloids, such as, for example, carboxymethylcellulose, natural and synthetic pulverulent, granular or latex-like polymers, such as gum arabic, polyvinyl alcohol, polyvinyl acetate, and natural phospholipids, such as cephalins and lecithins and synthetic phospholipid, and paraffin oils. The biocidal agents according to the invention can comprise here, for example, from 0.01 to 8% by weight, preferably from 0.05 to 4% by weight, particularly preferably from 02 to 3% by weight and very particularly preferably from 0.2 to 2% by weight, of adhesives.

Spreading agents, such as, for example, isopropyl myristate polyoxyethylene nonyl phenyl ether and polyoxyethylene lauryl phenyl ether. The biocidal agents according to the invention can comprise here, for example, from 0.01 to 20% by weight, preferably from 0.1 to 10% by weight, particularly preferably from 0.1 to 5% by weight and very particularly preferably from 0.1 to 2% by weight, of spreading agents.

Fragrances and dyes, such as, for example, inorganic pigments, for example iron oxide, titanium oxide, Prussian blue and organic dyes, such as alizarine, azo and metallophthalocyanine dyes and trace nutrients such as salts of iron, manganese, boron, copper, cobalt, molybdenum and zinc. The biocidal agents according to the invention can comprise here, for example, in each case from 0.001 to 4% by weight, preferably from 0.01 to 1% by weight, particularly preferably from 0.01 to 0.8% by weight, of fragrances and dyes.

Buffer substances, buffer systems or pH regulators. The biocidal agents according to the invention can comprise here, for example, in each case from 0.01 to 10% by weight, preferably from 0.1 to 5% by weight, of buffer substances, buffer systems or pH regulators.

Thickenings, such as, for example, polysaccharides, xanthan gum, sodium or magnesium silicates, heteropolysaccharides, alginates, carboxymethylcellulose, gum arabic or polyacrylic acids, preferably xanthan gum.

Dedusting agents are, for example, polyglycol s and polyglycol ethers. The biocidal agents according to the invention can comprise here, for example, in each case from 0.01 to 2% by weight, preferably from 0.05 to 1% by weight, particularly preferably from 0.1 to 0.5% by weight.

Flow agents or release agents that can be used are, for example, highly dispersed silica or Mg salts of fatty acids. The biocidal agents according to the invention can comprise here, for improving the flowability of the solids, in each case from 0.01 to 5% by weight, preferably from 0.05 to 3% by weight, particularly preferably from 0.1 to 2% by weight, of flow agent.

Pack preservatives are, for example, biocides, bactericides and fungicides. The biocidal agents according to the invention can comprise here, for example, in each case from 0.01 to 2% by weight, preferably from 0.05 to 1% by weight, of pack preservatives.

The total content of the aforementioned auxiliaries in the biocidal agents according to the invention is, for example, from 0.001 to 20% by weight, preferably from 0.1 to 15% by weight and particularly preferably from 0.1 to 10% by weight.

Solid formulations, such as, for example, powder mixtures or water-dispersible granules (WG) can comprise, besides the particulate microencapsulated iodopropargyl compounds, also solid auxiliaries such as, for example, natural stone flours, such as kaolins, clay earths, talc, marble, chalk, quartz, attapulgite, montmorillonite or diatomaceous earth or synthetic inorganic substances, such as highly dispersed silica, aluminium oxide and silicates, or mixtures thereof.

The solid formulations can be obtained in a manner known per se, for example by intimate mixing of the microcapsules according to the invention with the solid auxiliaries, or by combined comminution of solid auxiliaries with the microencapsulated iodopropargyl compounds. Furthermore, the solid formulations can be obtained by drying, for example spray drying, of a liquid formulation.

Preferred solid formulations comprise, for example, from 10 to 99.999% by weight of the microcapsules according to the invention, preferably from 15 to 99.9% by weight.

Liquid formulations can be, for example, suspension concentrates, dispersions, gels or pastes.

Preferred liquid formulations are preferably aqueous dispersions.

The liquid formulations such as, in particular, the dispersions can be prepared in a manner known per se, for example by jointly comminuting the further substances which are to be present in the liquid formulation and then adding the microencapsulated iodopropargyl compounds, or by mixing the microencapsulated iodopropargyl compounds and the other substances which are to be present in the liquid formulation intimately with one another by means of a dissolver or stirrer.

The liquid formulations comprise generally from 2 to 95% by weight, preferably from 5 to 75% by weight and very particularly preferably from 5 to 50% by weight, of the microcapsules according to the invention.

The invention furthermore relates to the use of the microcapsules according to the invention or of the biocidal agents according to the invention for the protection of technical materials, as well as to technical materials comprising the biocidal agents according to the invention or microcapsules according to the invention.

Technical materials are, for example, building materials, wood, woodbase materials, wood-plastic composite materials, sealing compositions, joint seals, plastics, films, stone slabs, textiles such as, for example, tarpaulins and tents, textile composite materials, coating compositions such as, for example, paints, wall paints, wood protection paints, façade paints, exterior paints, interior paints, emulsion paints, silicate paints, varnishes, concrete, cement, mortar or plaster, preferably silicate-bonded, mineral, resin-bonded or silicone-resin-bonded plasters, synthetic resin plasters, wood coatings, wood glazes, concrete coating, roof tile coatings, sealing compositions or textile coatings.

Further applications for coating compositions according to the invention are found, as well as in the building industry, also in medical technology, textile industry, rubber industry, sealant industry, agricultural industry and laboratory technology.

The advantage of the invention is considered to be that the microcapsules according to the invention exhibit a superior, i.e. reduced, leaching behaviour. According to the invention, it is thus possible to use both smaller quantitative amounts for the protection of coating compositions, as well as to achieve considerable longer action times.

The examples below illustrate the present invention.

EXAMPLES

Examples 1 to 4 describe the production of IPBC microcapsules.
The following materials were used herein:
Designation
Gum arabic solution (4% by weight)
Coadis™ BR3 (50% by weight in $H_2O$) (dispersion reagent; aqueous polyacrylate salt solution from Coatex)
SILFOAM®SRE (silicone antifoam emulsion defoamer from Wacker)
Preventol MP 100 (IPBC)
Maprenal®/water solution (1:1) (Maprenal® MF 921w/85WA melamine-formaldehyde polymer from INEOS Melamines)
Soprophor® S25 (emulsifier based on tris-steryl phenyl ether ethoxylates)
Preventol® BM 25 (pack preservative comprising 2.4% by weight of benzisothiazolinone and 4.9% by weight of methylisothiazolinone)
Rhodopol-G® (thickener based on xanthan gum from Solvay Rhodia)
Urea The size of the microcapsules was determined by means of laser diffraction. Either the solid capsules were added or suspensions/formulations produced therefrom. The following instruments and settings were used:
Instrument: LS 13 320 Particle Size Analyzer from Beckmann Coulter with PIDS technology (Polarization Intensity Differential Scattering Technology)
Sample module: Universal Liquid Module (ULM)
Illuminating Source: Diffraction: Solid State (780 nm); PIDS: tungsten lamp with band-pass filter (450, 600 and 900 nm)
Measuring time: 90 seconds, prior to the measurement 15 s ultrasound
Calculation: Fraunhofer model
Result: Diameter D50% and D90% of the volume distribution

Example 1

Production of IPBC-Containing Microcapsules (Post-Stirring Time 4 h at 70° C.)

In a 1 L stainless steel pot, 3.76 g of Coadis BR, 37.5 g of 4% strength by weight of gum arabic solution and 3.03 g of Wacker SRE antifoam were processed at room temperature in 637.22 g of water with stirring to give a slightly cloudy solution.

Then, by adding 8.85 g of a 50% strength by weight solution of citric acid in water the pH was lowered from pH=7.70 to pH=2.96.

The solution thus obtained was transferred to a 1000 ml flat-flange pot with impeller stirrer and Ultraturrax. With stirring using an impeller stirrer, 150.09 g of IPBC were added at approx. 400-420 rpm.

Then, the mixture was heated to 70° C., during which, above 60° C. and as the IPBC started to melt, the Ultra-Turrax was switched on (15 600 rpm) and, after reaching 70° C., the mixture was emulsified for at least 30 min.

Then, 150 g of a 50% strength by weight solution of Marprenai MF 921w/85WA in water were metered in over the course of 3 h. The Ultra-Turrax initially continued to run. After 10% of the melamine-formaldehyde polymer had been metered in, the Ultra-Turrax was switched off and the reaction mixture was stirred just using the impeller stirrer at an unchanged stirring speed.

Following the complete metered addition of the melamine-formaldehyde polymer, the reaction mixture was post-stirred for a further 4 h at 70° C., then left and filtered off with suction under membrane-pump vacuum. The moist filtercake was then washed with 67 g, 27 g and 7 g of hot (80° C.) water.

This gave 312.50 g of the white, moist product.
Product (T×T×t) from the start of the application: 70° C.×70° C.×7 h=34 300 (° C.)$^2$h
Product (T×T×t) after the end of the application: 70° C.×70° C.×4 h=19 600 (° C.)$^2$h
Particle size:
D50 [μm]: 29.9
D90 [μm]: 45.1

To determine the water and active ingredient content, a small sample was dried for 2 h on the Rotavapor and the IPBC content of the dried capsule mass was determined by means of IPBC.
Content of IPBC in the dry mass: 69.5% by weight
Particle size:
D50 [μm]: 24.0
D90 [μm]: 376

The moist product (entry 1a) and the dried capsules (entry 1b) were investigated as to their active ingredient release in water in the leaching test. The results are given in Table 1 below.

Example 2

Production of IPBC-Containing Microcapsules (Post-Stirring Time 4 h at 85° C.)

The microcapsules were produced analogously to Example 1, except that following complete metered addition of the melamine-formaldehyde polymer the reaction mixture was post-stirred for a further 4 h at 85° C.

This gave 312.50 g of the white, moist product.
Product (T×T×t) from the start of application:
70° C.×70° C.×3 h+85° C.×85° C.×4 h=43 600 (° C.)$^2$h
Product (T×T×t) after completion of the application: 85° C.×85° C.×4 h=28 900 (° C.)$^2$h
Particle size:
D50 [μm]: 22.3
D90 [μm]: 37.7

119.76 g of the moist product was dried on the Rotavapor. This gave 80.06 g of dried capsules as white powder with a IPBC content of 67.1% by weight.

Particle size:
D50 [μm]: 19.7
D90 [μm]: 34.6

The moist product (entry 2a) and the dried capsules (entry 2b) were investigated as to their active ingredient released in water in the leaching test. The results are given in Table 1 below.

Preparation of a Formulation from the Moist Product 151.35 g of water were stirred with 0.76 g of completely molten Soprophor S/25 using a propeller stirrer at approx. 300 rpm, then 84.22 g of the moist product were added and 0.25 g of 50% strength by weight NaOH solution was used to adjust the pH from 4.0 to 8.1. Then, 12.43 g of urea were added, the mixture was stirred for 10 minutes until everything had dissolved and then, with further stirring, 0.38 g of Rhodopol-G was slowly added and the mixture was stirred for 1 h until the formulation was homogeneous. The formulation was then preserved by adding 0.95 g of Preventol BM 25.

This gave 250 g of a white formulation with an IPBC content of 16.0% by weight.

Particle size:
D50 [μm]: 21.8
D90 [μm]: 57.9

The formulation was investigated as to its active ingredient release in water in the leaching test (entry 2c). The results are given in Table 1 below.

Preparation of a Formulation from the Dried Capsules 178.0 g of water were stirred with 0.76 g of completely molten Soprophor S/25 using a propeller stirrer at approx. 300 rpm, then 55.88 g of the dried capsules were added and 0.23 g of 50% strength by weight NaOH solution was used to adjust the pH to 8.3. Then, 12.49 g of urea were added, the mixture was stirred for 10 minutes until everything had dissolved and then, with further stirring, 0.40 g of Rhodopol-G was slowly added and stirring was carried out for 1 h until the formulation was homogeneous. The formulation was then preserved by adding 0.95 g of Preventol BM 25.

This gave 250 g of a white formulation with an IPBC content of 13.6% by weight.

Particle size:
D50 [μm]: 20.4
D90 [μm]: 37.5

The formulation was investigated as to its active ingredient release in water in the leaching test (entry 2d). The results are given in Table 1 below.

Example 3

Production of IPBC-Containing Microcapsules (Post-Stirring Time 18 h at 80° C.)

The microcapsules were produced analogously to Example 1 except that following complete metered addition of the melamine-formaldehyde polymer the reaction mixture was post-stirred for a further 18 h at 80° C.

This gave 253.98 g of the white, moist product. The content of IPBC was 50.2% by weight.

Product (T×T×t) from the start of application:
70° C.×70° C.×3 h+85° C.×85° C.×18 h=144 750 (° C.)²h
Product (T×T×t) after completion of the application: 85° C.×85° C.×18 h=130 050 (° C.)²h Particle size:
D50 [μm]: 192
D90 [μm]: 39.4

123.95 g of the moist product were dried on the Rotavapor. This gave 91.92 g of dried capsules as white powder with an IPBC content of 67.7% by weight.

Particle size:
D50 [μm]: 19.3
D90 [μm]: 33.7

The moist product (entry 3a) and the dried capsules (entry 3b) were investigated as to their active ingredient release in water in the teaching test. The results are given in Table 1 below.

Preparation of a Formulation from the Moist Product 160 g of water were stirred with 0.76 g of completely molten Soprophor S/25 using a propeller stirring at approx. 300 rpm, then 75.11 g of the moist product were added and 0.24 g of 50% strength by weight NaOH solution was used to adjust the pH from 4.0 to 8.8. Then, 12.52 g of urea were added, the mixture was stirred for 10 minutes with everything had dissolved and then, with further stirring, 0.38 g of Rhodopol-G was slowly added and the mixture was stirred for 1 h until the formulation was homogeneous. The formulation was then preserved by adding 0.95 g of Preventol BM 25.

This gave 250.3 g of a white formulation with an IPBC content of 141% by weight.

Particle size:
D50 [μm]: 21.4
D90 [μm]: 81.2

The formulation was investigated as to its active ingredient release in water in the leaching test (entry 3c). The results are given in Table 1 below, Preparation of a Formulation from the Dried Capsules 178.5 g of water were stirred with 0.80 g of completely molten Soprophor S/25 using a propeller stirrer at approx. 300 rpm, then 55.53 g of the dried capsules were added and 0.95 g of 1 M NaOH solution was used to adjust the pH to 8.3. Then, 12.49 g of urea were added and the mixture was stirred for 10 minutes until everything had dissolved and then, with further stirring, 0.38 g of Rhodopol-G was slowly added and the mixture was stirred for 1 h until the formulation was homogeneous. The formulation was then preserved by adding 0.95 g of Preventol BM 25.

This gave 250.2 g of a white formulation with a content of IPBC of 15.8% by weight.

Particle size:
D50 [μm]; 20.4
D90 [μm]: 36.1

The formulation was investigated as to its active ingredient release in water in the leaching test (entry 3d). The results are given in Table 1 below.

Example 4

Production of IPBC-Containing Microcapsules (Post-Stirring Time 22.5 h at 80° C., with Sodium Sulphate)

The microcapsules were produced analogously to Example 1, except that following complete metered addition of the melamine-formaldehyde polymer the reaction mixture was post-stirred for a further 20 h at 80° C. and following the addition of 99.1 g of sodium sulphate, for a further 2.5 h at 80° C.

Product (T×T×t) from the start of application:
70° C.×70° C.×3 h+85° C.×85° C.×22.5 h=177 262.5 (° C.)²h
Product (T×T×t) following completion of the application:
85° C.×85° C.×22.5 h=162 562.5 (° C.)²h To produce a moist product and a formulation, the still-hot mixture was divided.

Preparation of the Moist Product 519.07 g of the mixture were let out and filtered with suction under membrane-pump vacuum. The moist filtercake was then washed with 52 g, 52 g and 26 g of hot (80° C.) water. The mixture was then suction dried for a further 15 minutes.

This gave 152.12 g of moist product.
Particle size:
D50 [μm]: 22.2
D90 [μm]: 78.9

To determine the water and active ingredient content, a email sample was dried on the Rotavapor for 2 h at 80° C. and 80 mbar and the IPBC content of the dried capsule mass was determined by means of IPBC.

Content of IPBC in the dry mass: 68.4% by weight
Particle size:
D50 [μm]: 21.1
D90 [μm]: 61.9

The moist product (entry 4a) and the dried capsules (entry 4b) were investigated as to their active ingredient released in water in the leaching test. The results are given in Table 1 below.

Preparation of a Formulation from the Reaction Suspension 435.80 g of the remaining suspension were admixed, with stirring, with 5.51 g of a 33% strength by weight solution of Soprophor S/25 in water. Then, 1.38 g of a 40% strength by weight NaOH solution was used to adjust the pH from 4.03 to 8,46. With further stirring, 21.79 g of urea and 2.46 g of Rhodopol G were then added and the mixture was stirred for a further 2 h until homogeneous. This gave 466.95 g of a white suspension with a content of IPBC of 12.1% by weight (HPLC).

Particle size:
D50 [μm]: 20.3
D90 [μm]: 34.3

The formulation was investigated as to its active ingredient release in water in the leaching test (entry 4c). The results are given in Table 1 below.

Preparation of a Formulation from the Moist Filtercake 300.0 g of water are stirred with 1.43 g of completely molten Soprophor S/25 with a propeller stirrer at approx. 300 rpm, then 143.38 g of the moist filtercake From Example 1 a are added and 0.7 g of 50% strength NaOH solution is used to adjust the pH from 4.2 to 7.2. Then, 23.75 g of urea are added, and the mixture is stirred for 10 minutes until everything has dissolved and then, with further stirring, 0.71 g of Rhodopol-G is slowly added and the mixture is stirred for 2 h until the formulation is homogeneous. The formulation is then preserved by adding 0.95 g of Preventol BM 25 (preservative of 2.4% benzisothiazolinone and 4.9% methylisothiazolinone).

This gives 478.72 g of a white formulation with a content of IPBC of 14.6%.

Particle size:
D50 [μm]: 19.4
D90 [μm]: 31.6

The formulation was investigated as to its active ingredient release in water in the leaching test (entry 4d). The results are given in Table 1 below.

Example 5 (Comparative Experiment Analogous to Preparation Example 3 from WO 2004000953)

In a 1 L stainless steel pot, 0.99 g of gum arabic, 4.99 g of Wacker SRE antifoam and 272.50 g of Preventol MP 400 (40% strength suspension of IPBC in water) were stirred into 394.9 g of water. Then, the pH was adjusted from 3.91 to 2.09 by adding 99 g of 12% strength by weight citric acid. The dispersion was heated to 60° C. and, with stirring, 217 g of a 50% strength by weight solution of Marprenal MP 921w/85WA in water were metered in over the course of 1 h. Then, the mixture was post-stirred for 2 h at 60° C.

144 g of the capsule dispersion were filtered off and washed with 25 g and 20 g of cold water. This gave 40.15 g of moist filtercake with an IPBC content of 34.7% by weight.

4.67 g of the moist filtercake were dried on the Rotavapor. This gave 2.90 g of a white powder with an IPBC content of 55.9% by weight.

Product (T×T×t) from the start of application: 60° C.×60° C.×3 h=10 800 (° C.)²h Product (T×T×t) after the end of application: 60° C.×60° C.×2 h=7 200 (° C.)²h Both samples were investigated as regards theft leaching behaviour (see Table 1).

Carrying Out the Leaching Test for IPBC-Containing Microcapsules

In a 100 ml screw-top glass jar, an amount of the formulation was weighed in which comprises 280 ppm of IPBC (based on 100 g), and topped up to 100 g with water. The screw-top jar was closed and the sample was shaken on a circular shaker at 250 revolutions per minute and 20° C. After 24 hours (24 h leaching test) and 72 hours (72 h leaching test), 1 ml sample was removed using a pipette and transferred to a reaction vessel. The sample was centrifuged for 6 minutes at 14 000 revolutions per minute and the supernatant was analyzed by means of High Performance Liquid Chromatography.

The solubility of IPBC in pure water is 135 ppm, although it may also be greater in the test medium due to microcapsule or formulation constituents.

TABLE 1

| Entry/Example | 24 h | 72 h |
|---|---|---|
| 1a | 16.6 ppm | 46.1 ppm |
| 1b | 26.5 ppm | 57.1 ppm |
| 2a | 19.3 ppm | 28.7 ppm |
| 2b | 19.9 ppm | 26.4 ppm |
| 2c | 23.6 ppm | 35.6 ppm |
| 2d | 23.5 ppm | 24.5 ppm |
| 3a | 14.2 ppm | 15.2 ppm |
| 3b | 17.5 ppm | 18.9 ppm |
| 3c | 18.0 ppm | 20.2 ppm |
| 3d | 23.8 ppm | 34.2 ppm |
| 4a | 10.8 ppm | 11.3 ppm |
| 4b | 13.2 ppm | 15.2 ppm |
| 4c | 12.4 ppm | 14.3 ppm |
| 4d | 9.9 ppm | 11.4 ppm |
| 5a | 131.1 | 180.3 |
| 5b | 108.5 | 162.0 |

What is claimed is:

1. Microcapsules comprising at least one biocidal iodopropargyl compound microencapsulated with a microencapsulation material which comprises at least 95% of a melamine-formaldehyde polymer, wherein weight ratio of the microencapsulation material to the at least one iodopropargyl compound is 1:1.5 to 1:10.

2. The microcapsules according to claim 1, wherein the iodopropargyl compound comprises 3-iodo-2-propynyl butylcarbamate.

3. The microcapsules according to claim 1, wherein the microcapsules have a volume-average particle size of 0.3 to 100 μm.

4. The microcapsules according to claim 1, wherein the microcapsules have a D90 value, determined by a laser diffraction, of 90 μm or less.

5. The microcapsules according to claim 1, wherein the microencapsulation material comprises an additional material selected from the group consisting of synthetic, semisynthetic or natural polymers.

6. The microcapsules according to claim 1, wherein the microcapsules have a weight ratio of the microencapsulation material to the at least one iodopropargyl compound of 1:10 to 1:2.

7. The microcapsules according to claim 1, wherein the microcapsules have a 24 h leaching rate of 1 to 80 parts per million (ppm).

8. The microcapsules according to claim 1, wherein:
the biocidal Iodopropargyl compound comprises at least one compound selected from the group consisting of 3-iodo-2-propynyl propylcarbamate, 3-iodo-2-propynyl butylcarbamate (IPBC), 3-iodo-2-propynyl m-chlorophenyicarbamate, 3-iodo-2-propynyl phenyicarbamate, 3-iodo-2-propynyl 2,4,5-trichlorophenyl ether, 3-iodo-2-propynyl 4-chlorophenyl formal (IPCF), di-(3-iodo-2-propynyl)hexyl dicarbamate, 3-iodo-2-propynyl oxyethanol ethylcarbamate, 3-iodo-2-propynyl oxyethanol phenyicarbamate, 3-iodo-2-propynyl thioxothio-ethylcarbamate, 3-iodo-2-propynyl carbamic acid ester (IPC), N-iodopropargyl-oxycarbonylalanine, N-iodopropargyloxycarbonylalanine ethyl ester, 3-(3-iodo-propargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-bromo-2,3-diiodo-2-propenylethyl carbamate, 3-iodo2-propynyl-n-hexyl carbamate, and 3-iodo-2-propynyl cyclohexyl carbamate; and
the microcapsules have:
a volume-average particle size of 5 to 60 µm;
a D90 value, determined by a laser diffraction, of 10 to 60 µm; and
a weight ratio of the microencapsulation material to the at least one iodopropargyl compound of 1:10 to 1:2.

9. The microcapsules according to claim 8, wherein:
the microencapsulation material comprises at least 95% by weight of the at least one melamine-formaldehyde polymer; and
the microencapsulation material comprises an additional material selected from the group consisting of synthetic, semisynthetic or natural polymers.

10. The microcapsules according to claim 9, wherein:
the microcapsules have a 24 h leaching rate of 5 to 40 ppm determined by means of 24 h leaching test;
the iodopropargyl compound comprises 3-iodo-2-propynyl butylcarbamate; and
the additional material comprises an aminoplastic resin.

11. The microcapsules according to claim 1, wherein the weight ratio of the microencapsulation material to the at least one iodopropargyl compound is 1:4 to 1:2.

12. The microcapsules according to claim 6, wherein the microencapsulation material comprises at least 99% by weight of the at least one melamine-formaldehyde polymer.

13. A biocidal agent comprising the microcapsules according to claim 1.

14. A process for producing the microcapsules according to claim 1, the process comprising:
a) applying the microencapsulation material to the at least one iodopropargyl compound to form coated compound; and
b) treating the coated compound at a temperature T of 50 to 95° C., over a period t, such that T×T×t is>18,000 (° C.)²h.

15. The process according to claim 14, wherein applying the microencapsulation material comprises:
contacting an aqueous emulsion or suspension of the at least one iodopropargyl compound with the at least one melamine-formaldehyde polymer, and
reducing the solubility of the least one melamine-formaldehyde polymer in the aqueous solution.

16. The process according to claim 15, wherein reducing the solubility comprises at least one of increasing the electrolyte content or adjusting the pH to a pH of less than 6.5.

17. The process according to claim 14 wherein T×T×t refers to a period and temperature after the application of the microencapsulation material has ended, the temperature T is 70 to 90° C., and T×T×t is>25,000 (° C.)²h.

18. A method for controlling microorganisms on technical materials or for protecting technical materials against change by or infestation with microorganisms, the method comprising contacting technical material with the microcapsules according to claim 1.

19. The method according to claim 18, wherein the technical materials are building materials, wood, woodbase materials, wood/plastic composite materials, sealing compositions, plastics, films, stone slabs, textiles, textile composite materials or coating compositions.

* * * * *